United States Patent [19]

Keil et al.

[11] Patent Number: 5,554,582
[45] Date of Patent: Sep. 10, 1996

[54] CYCLOHEXENONE COMPOUNDS, THEIR PREPARATION AND THEIR USE FOR CONTROLLING UNDESIRABLE PLANT GROWTH

[75] Inventors: Michael Keil, Freinsheim; Ulrich Schirmer, Heidelberg; Dieter Kolassa, Ludwigshafen; Juergen Kast, Boehl-Iggelheim; Bruno Wuerzer, Otterstadt; Norbert Meyer, Ladenburg, all of Germany

[73] Assignee: BASF Aktiengesellschaft, Ludwigshafen, Germany

[21] Appl. No.: 983,604

[22] Filed: Nov. 30, 1992

Related U.S. Application Data

[63] Continuation of Ser. No. 545,764, Jun. 29, 1990, abandoned, which is a continuation of Ser. No. 281,999, Dec. 9, 1988, abandoned.

[30] Foreign Application Priority Data

Dec. 10, 1987 [DE]  Germany .......................... 37 41 823.8

[51] Int. Cl.$^6$ .......................... A01N 33/24; A01N 43/32; A01N 43/18; C07C 251/44
[52] U.S. Cl. .......................... 504/344; 504/288; 504/790; 504/293; 549/13; 549/22; 549/39; 549/426; 564/256
[58] Field of Search ...................... 504/344, 288, 504/290, 293; 564/256; 549/13, 22, 39, 426

[56] References Cited

U.S. PATENT DOCUMENTS

| | | | |
|---|---|---|---|
| 3,950,420 | 4/1976 | Sawaka et al. | 260/563 |
| 3,989,737 | 11/1976 | Sawaki et al. | 564/256 |
| 4,011,256 | 3/1977 | Sawaki et al. | |
| 4,075,239 | 3/1978 | Sawaki et al. | |
| 4,482,740 | 11/1984 | Iwataki et al. | |
| 4,504,305 | 3/1985 | Iwataki et al. | |
| 4,666,510 | 5/1987 | Watson et al. | 71/121 |
| 4,898,610 | 2/1990 | Keil et al. | 71/121 |

FOREIGN PATENT DOCUMENTS

| | | | |
|---|---|---|---|
| 0556148 | 10/1986 | Australia | 564/256 |
| 0133349 | 2/1985 | European Pat. Off. | 564/256 |
| 2439104 | 3/1975 | Germany . | |
| 3248554 | 7/1983 | Germany . | |
| 3329017 | 2/1985 | Germany . | |
| 2137200 | 10/1984 | United Kingdom | 564/256 |

OTHER PUBLICATIONS

U.S. Application U.S. Ser. No. 639,473 Keil et al.=DE 33 29 017.

Primary Examiner—Peter O'Sullivan
Attorney, Agent, or Firm—Keil & Weinkauf

[57] ABSTRACT

Cyclohexenone compounds of the formula

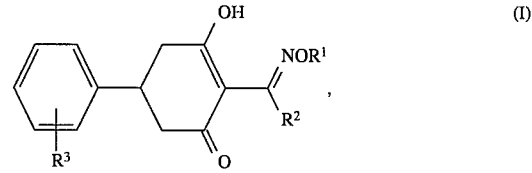

where $R^1$ is alkyl of 1 to 4 carbon atoms, alkenyl or alkynyl of 3 or 4 carbon atoms, haloalkenyl of 3 or 4 carbon atoms and 1 to 3 halogen substituents, or is thenyl which is unsubstituted or substituted by halo and/or alkyl, $R^2$ is alkyl of 1 to 4 carbon atoms, and $R^3$ is formyl, a radical of the general formula $R^4XCHXR^5$, where X is oxygen or sulfur, and $R^4$ and $R^5$ are identical or different alkyl, or together denote alkylene of 1 to 4 carbon atoms and which is unsubstituted or substituted by alkyl, alkoxy, alkylthio, hydroxy, halogen, cyano or N,N-dialkylamino, have a good herbicidal action preferably on species from the grass family.

5 Claims, No Drawings

CYCLOHEXENONE COMPOUNDS, THEIR PREPARATION AND THEIR USE FOR CONTROLLING UNDESIRABLE PLANT GROWTH

This application is a continuation of application Ser. No. 07/545,764, filed on Jun. 29, 1990, now abandoned, which is a continuation of Ser. No. 07/281,999, filed Dec. 9, 1988, now abandoned.

The present invention relates to cyclohexenone compounds, processes for their preparation and herbicides which contain these compounds as active ingredients.

It is known that cyclohexenone compounds can be used for controlling undesirable grasses in broad-leaved crops (German Laid-Open Application DOS 2,439,104). Furthermore, German Laid-Open Applications DOS 3,248,554 and DOS 3,329,017 disclose that cyclohexen-1-one compounds which carry a para-substituted phenyl radical in the 5-position control gramineous weeds in wheat.

We have found that cyclohexenone compounds of the formula I

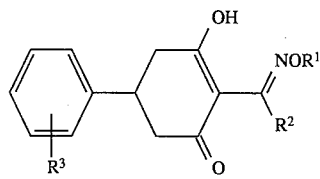
(I)

where $R^1$ is alkyl of 1 to 4 carbon atoms, alkenyl or alkynyl of 3 or 4 carbon atoms, haloalkenyl having 3 or 4 carbon atoms and 1 to 3 halogen substituents or thienyl which is unsubstituted or monosubstituted, disubstituted or trisubstituted by halogen and/or $C_1$–$C_4$-alkyl, $R^2$ is alkyl of 1 to 4 carbon atoms and $R^3$ is formyl or a radical of the general formula $R^4XCHXR^5$, where X is O or S and $R^4$ and $R^5$ are identical or different alkyl radicals or together form alkylene of 1 to 4 carbon atoms and which may additionally be substituted by $C_1$–$C_4$-alkyl, $C_1$–$C_4$-alkoxy, $C_1$–$C_4$-alkylthio, hydroxyl, halogen, cyano or $C_1$–$C_4$-N,N-dialkylamino, and their biologically acceptable salts with alkali metal, alkaline earth metal and ammonium ions and their esters with $C_1$–$C_{10}$-carboxylic acids and inorganic acids have a good herbicidal action, preferably against species from the grass family (Gramineae). They are tolerated and therefore selective in broad-leaved crops and in monocotyledon plants which do not belong to the Gramineae. Some compounds also show selective behavior in crops of Gramineae, for example wheat, barley or rice, in the sense that they control un desirable grasses without significantly damaging the useful crops.

Formula I gives only one of the possible tautomeric forms; there are also many other possible forms, all of which are intended to be embraced by the general formula I, as shown below.

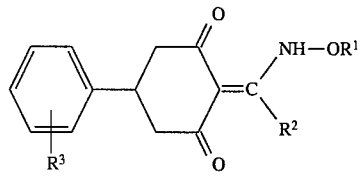

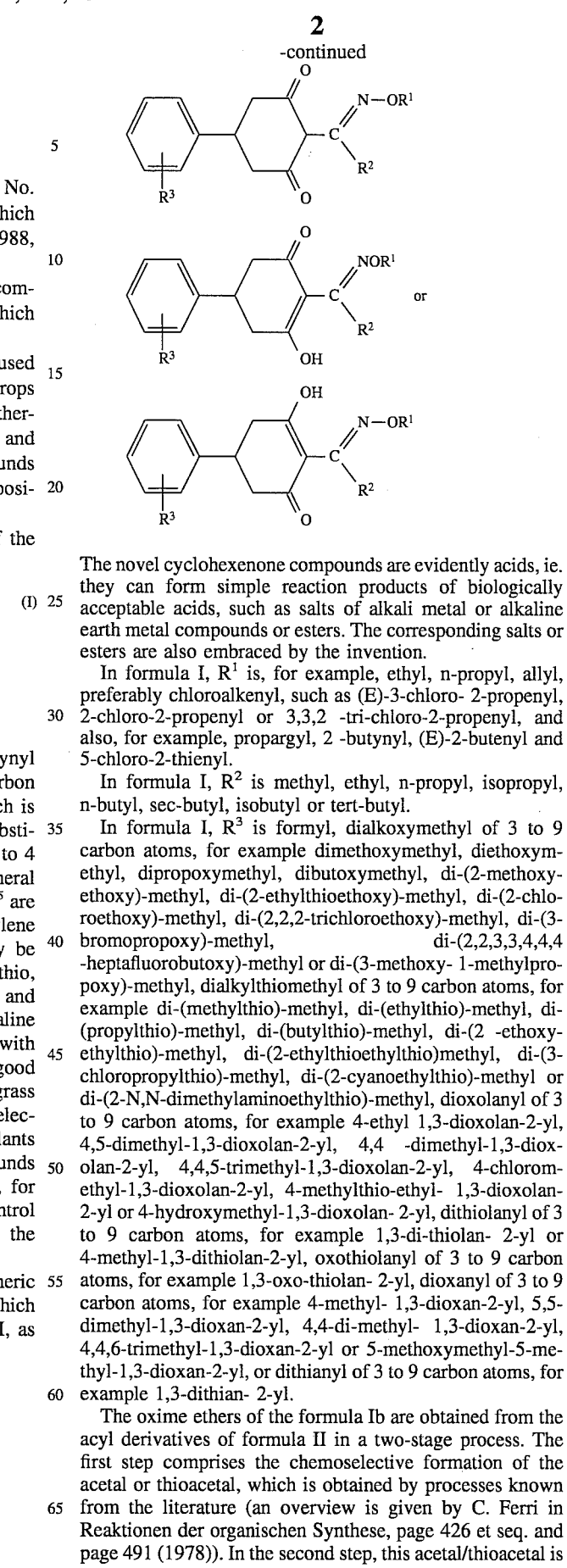

The novel cyclohexenone compounds are evidently acids, ie. they can form simple reaction products of biologically acceptable acids, such as salts of alkali metal or alkaline earth metal compounds or esters. The corresponding salts or esters are also embraced by the invention.

In formula I, $R^1$ is, for example, ethyl, n-propyl, allyl, preferably chloroalkenyl, such as (E)-3-chloro- 2-propenyl, 2-chloro-2-propenyl or 3,3,2 -tri-chloro-2-propenyl, and also, for example, propargyl, 2 -butynyl, (E)-2-butenyl and 5-chloro-2-thienyl.

In formula I, $R^2$ is methyl, ethyl, n-propyl, isopropyl, n-butyl, sec-butyl, isobutyl or tert-butyl.

In formula I, $R^3$ is formyl, dialkoxymethyl of 3 to 9 carbon atoms, for example dimethoxymethyl, diethoxymethyl, dipropoxymethyl, dibutoxymethyl, di-(2-methoxyethoxy)-methyl, di-(2-ethylthioethoxy)-methyl, di-(2-chloroethoxy)-methyl, di-(2,2,2-trichloroethoxy)-methyl, di-(3-bromopropoxy)-methyl, di-(2,2,3,3,4,4,4 -heptafluorobutoxy)-methyl or di-(3-methoxy- 1-methylpropoxy)-methyl, dialkylthiomethyl of 3 to 9 carbon atoms, for example di-(methylthio)-methyl, di-(ethylthio)-methyl, di-(propylthio)-methyl, di-(butylthio)-methyl, di-(2 -ethoxyethylthio)-methyl, di-(2-ethylthioethylthio)methyl, di-(3-chloropropylthio)-methyl, di-(2-cyanoethylthio)-methyl or di-(2-N,N-dimethylaminoethylthio)-methyl, dioxolanyl of 3 to 9 carbon atoms, for example 4-ethyl 1,3-dioxolan-2-yl, 4,5-dimethyl-1,3-dioxolan-2-yl, 4,4 -dimethyl-1,3-dioxolan-2-yl, 4,4,5-trimethyl-1,3-dioxolan-2-yl, 4-chloromethyl-1,3-dioxolan-2-yl, 4-methylthio-ethyl- 1,3-dioxolan-2-yl or 4-hydroxymethyl-1,3-dioxolan- 2-yl, dithiolanyl of 3 to 9 carbon atoms, for example 1,3-di-thiolan- 2-yl or 4-methyl-1,3-dithiolan-2-yl, oxothiolanyl of 3 to 9 carbon atoms, for example 1,3-oxo-thiolan- 2-yl, dioxanyl of 3 to 9 carbon atoms, for example 4-methyl- 1,3-dioxan-2-yl, 5,5-dimethyl-1,3-dioxan-2-yl, 4,4-di-methyl- 1,3-dioxan-2-yl, 4,4,6-trimethyl-1,3-dioxan-2-yl or 5-methoxymethyl-5-methyl-1,3-dioxan-2-yl, or dithianyl of 3 to 9 carbon atoms, for example 1,3-dithian- 2-yl.

The oxime ethers of the formula Ib are obtained from the acyl derivatives of formula II in a two-stage process. The first step comprises the chemoselective formation of the acetal or thioacetal, which is obtained by processes known from the literature (an overview is given by C. Ferri in Reaktionen der organischen Synthese, page 426 et seq. and page 491 (1978)). In the second step, this acetal/thioacetal is reacted with an appropriate hydroxylamine salt $R^1ONH_3Y$, where Y is any anion, to give the oxime ether of the formula Ib.

dichloroethane, hexane or cyclohexane, esters, such as ethyl acetate, and ethers, such as dioxane or tetrahydrofuran.

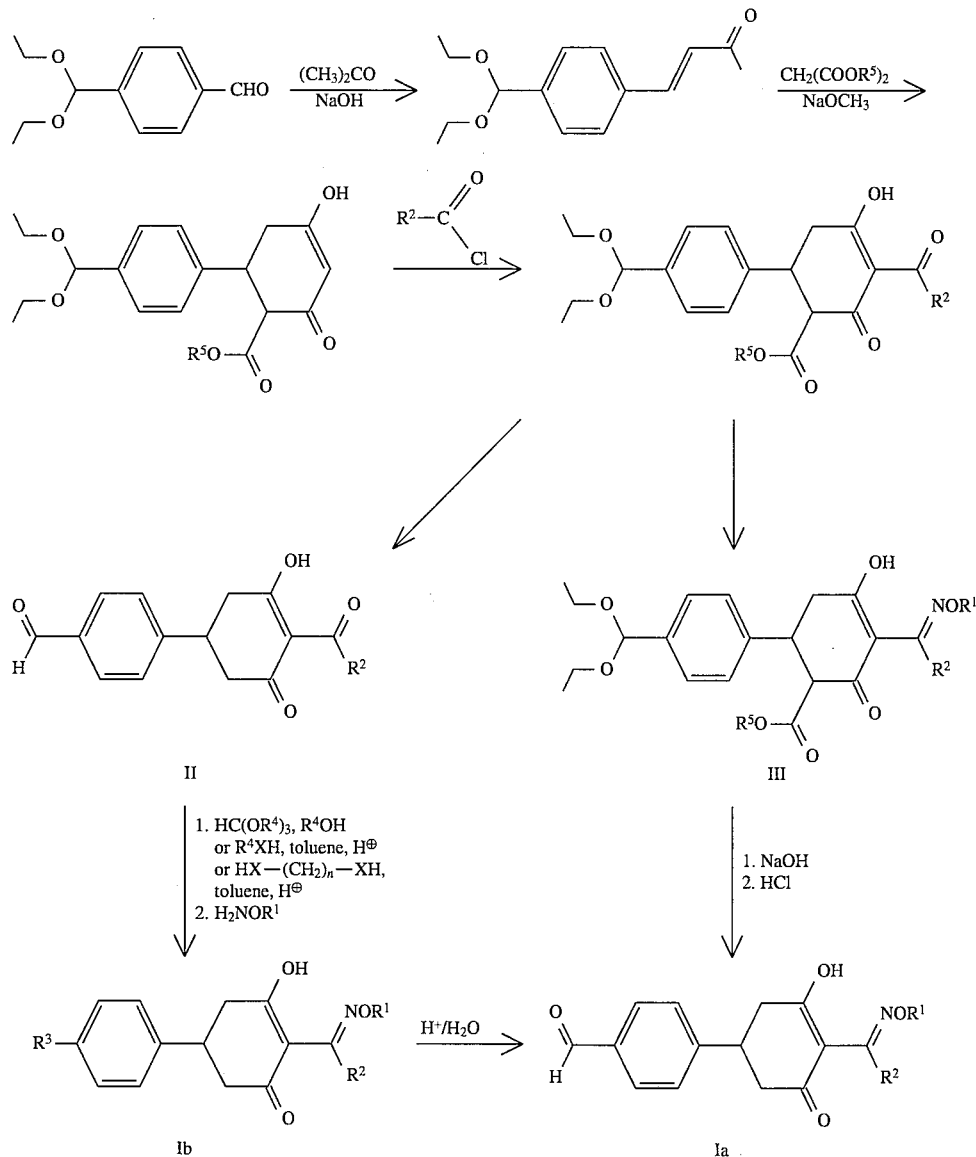

This reaction is advantageously carried out in the heterogeneous phase in a diluent at an adequate temperature above 0° C. and below the boiling point of the reaction mixture, in the presence of a base. Examples of suitable bases are carbonates, bicarbonates, acetates, alcoholates, hydroxides or oxides of alkali or alkaline earth metals, in particular of sodium, potassium, magnesium or calcium. Organic bases, such as pyridine or tertiary amines, can also be used.

The reaction takes place particularly readily at a pH of from 2 to 9, in particular from 4.5 to 5.5. The pH is advantageously obtained by adding an acetate buffer, for example sodium acetate or potassium acetate, or a mixture of the two salts. Alkali metal acetates are added, for example, in amounts of from 0.5 to 2 moles, based on the ammonium compound of the formula $R^1O$—$NH_3Y$.

Examples of suitable solvents are dimethyl sulfoxide, alcohols, such as methanol, ethanol or isopropanol, benzene, hydrocarbons and chlorohydrocarbons, such as chloroform, The reaction is complete after a few hours, after which the reaction product can be isolated by evaporating down the mixture, adding water and extracting with a nonpolar solvent, such as methylene chloride, and distilling off the solvent under reduced pressure.

Compounds of the formula I can also be obtained by reacting corresponding compounds of the formula II with the appropriate free hydroxylamine $R^1O$—$NH_2$ in a diluent at from 0° C. to the boiling point of the reaction mixture, in particular from 15° to 70° C. If necessary, the hydroxylamine can be used in the form of an aqueous solution.

Suitable solvents for this reaction are, for example, alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic esters, such as tetrahydrofuran.

The compounds of the formula Ia where $R^3$ is formyl are obtained, for example, by hydrolyzing the acetal esters III ($R^3$=dialkoxymethyl) by means of an aqueous alkali metal hydroxide solution, for example sodium hydroxide solution or potassium hydroxide solution, at from 0° to 100° C., preferably at room temperature. On subsequent acidification to pH 1–5 with a conventional acid, for example hydrochloric acid, sulfuric acid, phosphoric acid, acetic acid, oxalic acid or formic acid, the desired aldehyde is formed with simultaneous decarboxylation and cleavage of the acetal, and is, if required, isolated by extraction. Suitable extracting here are all organic solvents which are not miscible with water, for example toluene, dichloromethane or ethyl acetate.

Compounds of the formula Ia can also be obtained by cleavage of the acetals and thioacetals of the formula The conventional processes are documented in detail Th. W. Greene Protective Groups in Organic Synthesis, pages 115–138 (1981).

EXAMPLE 1

5-(4-dimethoxymethylphenyl)-2-(1-ethoxyiminobutyl)-4-hydroxycyclohex-2-en-1-one 2.5 g of ethoxyamine, 2.1 g of sodium bicarbonate and 100 ml of methanol are added to 8.4 g of 2-butyryl-5-(4-dimethoxymethylphenyl)-3-hydroxycyclohex-2-en-1-one and the mixture is stirred for 10 hours at room temperature. After the mixture has been evaporated down, the residue is partitioned in methylene chloride/water, and the organic phase is separated off, dried and evaporated down. 7.5 g of 5-(4-dimethoxymethylphenyl)-2-(1 -ethoxyiminobutyl)-3-hydroxycyclohex-2-en-1-one (compound No. 19 in the Table below) remain:

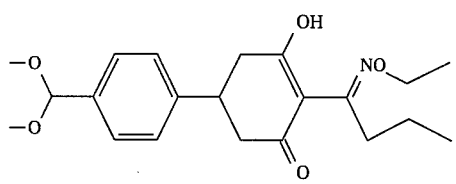

EXAMPLE 2

2-(1-Ethoxyiminobutyl)-5-(4-formylphenyl)-3-hydroxycyclohex-2-en-1-one 2.0 g of the compound No. 19 (Example 1) were treated with a mixture of 3.5 g of silica gel (70–270 mesh), 5 ml of dichloromethane and 0.35 g of 10% strength oxalic acid for 15 hours at room temperature. The mixture was filtered, the residue was washed with dichloromethane and the filtrate was evaporated down. 1.5 g of 2-(1-ethoxyiminobutyl)-5-(4-formylphenyl)-3-hydroxycyclo-hex- 2-en-1-one remain as a solid of melting point 81°–82° C. (compound No. 8).

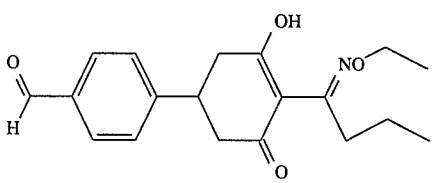

The compounds listed in the table below can be prepared from suitable intermediates, if necessary after slight adaptation of the above examples; they are expected to have a similar action. A typical selection of compounds (characterized by physical data) was prepared and investigated for biological activity.

TABLE

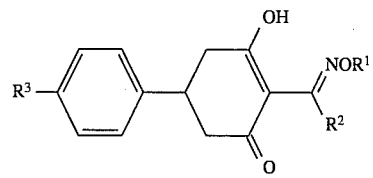

(I)

| Comp. no. | $R^3$ | $R^2$ | $R^1$ | m.p. [°C.] or characteristic $^1$H-NMR data [δ ppm] |
|---|---|---|---|---|
| 1 | CHO | $C_2H_5$ | $C_2H_5$ | 1.17(t), 1.33(t), 2.97(q), 4.13(q), 10.0(s) |
| 2 | CHO | $C_2H_5$ | n-$C_3H_7$ | 1.0(t), 2.96(t), 3.10(q), 4.03(t), 10.0(s) |
| 3 | CHO | $C_2H_5$ | $CH_2-CH=CH_2$ | 1.18(t), 2.97(t), 4.58(d), 10.01(s) |
| 4 | CHO | $C_2H_5$ | (E)$-CH_2-CH=CHCl$ | 1.17(t), 2.92(q), 4.55(d), 6.12(m), 6.36(d), 10.0(s) |
| 5 | CHO | $C_2H_5$ | (E)$-CH_2-CH=CH-CH_3$ | 1.18(t), 1.78(d), 2.97(q), 4.47(d), 10.0(s) |
| 6 | CHO | $C_2H_5$ | $CH_2-C\equiv CH$ | 1.16(t), 2.90(q), 4.67(d), 10.01(s) 114–16 |
| 7 | CHO | $C_2H_5$ | $CH_2-C\equiv C-CH_3$ | |
| 8 | CHO | n-$C_3H_7$ | $C_2H_5$ | 81–82 |
| 9 | CHO | n-$C_3H_7$ | n-$C_3H_7$ | 0.99(t); 4.03(t); 10.01(s) 66–68 |
| 10 | CHO | n-$C_3H_7$ | $CH_2-CH=CH_2$ | 1.01(t); 5.96(m); 10.01(s) 63–64 |
| 11 | CHO | n-$C_3H_7$ | (E)$-CH_2-CH=CHCl$ | 0.99(t); 6.11(m); 6.36(d) |
| 12 | CHO | n-$C_3H_7$ | (E)$-CH_2-CH=CH-CH_3$ | |

TABLE-continued $$\text{(I)}$$

Structure: 4-R³-phenyl substituted cyclohexenone with OH, NOR¹, R² and =O groups.

| Comp. no. | R³ | R² | R¹ | m.p. [°C.] or characteristic ¹H-NMR data [δ ppm] |
|---|---|---|---|---|
| 13 | CHO | n-C₃H₇ | CH₂—C≡CH | 0.98(t), 2.65(s), 4.67(d), 10.01(s) 72–73 |
| 14 | CHO | n-C₃H₇ | CH₂—C≡C—CH₃ | 68–70 |
| 15 | CH(OCH₃)₂ | C₂H₅ | C₂H₅ | 1.19(t), 1.33(t), 2.97(q), 3.34(s), 4.15(q), 5.37(s) |
| 16 | CH(OCH₃)₂ | C₂H₅ | CH₂—CH=CH₂ | 1.18(t), 2.95(q), 3.32(s), 4.55(d), 5.36(dd) |
| 17 | CH(OCH₃)₂ | C₂H₅ | (E)—CH₂—CH=CHCl | 1.16(t), 2.91(q), 3.33(s), 4.53(d), 5.39(s) |
| 18 | CH(OCH₃)₂ | C₂H₅ | (E)—CH₂—CH=CH—CH₃ | 1.17(t), 1.77(d), 2.96(q), 3.33(s), 4.48(d), 5.38(s) |
| 19 | CH(OCH₃)₂ | n-C₃H₇ | C₂H₅ | 0.98(t); 3.33(s); 4.10(s) |
| 20 | CH(OCH₃)₂ | n-C₃H₇ | CH₂—CH=CH₂ | 0.99(t), 2.95(t), 3.33(s), 4.55(d), 5.35(dd), 5.36(s) |
| 21 | CH(OCH₃)₂ | n-C₃H₇ | (E)—CH₂—CH=CHCl | 0.99(t), 3.33(s), 4.53(d), 5.38(s) |
| 22 | CH(OCH₃)₂ | n-C₃H₇ | (E)—CH₂—CH=CH—CH₃ | 1.0(t), 1.78(d), 3.34(s), 5.39(s) |
| 23 | CH(OC₂H₅)₂ | C₂H₅ | C₂H₅ | 2.97(q), 4.15(q), 5.5(s) |
| 24 | CH(OC₂H₅)₂ | C₂H₅ | CH₂—CH=CH₂ | |
| 25 | CH(OC₂H₅)₂ | C₂H₅ | (E)—CH₂—CH=CHCl | |
| 26 | CH(OC₂H₅)₂ | C₂H₅ | (E)—CH₂—CH=CH—CH₃ | |
| 27 | CH(OC₂H₅)₂ | n-C₃H₇ | C₂H₅ | 0.99(t), 1.23(t), 1.32(t), 4.12(q), 5.5(s) |
| 28 | CH(OC₂H₅)₂ | n-C₃H₇ | CH₂—CH=CH₂ | |
| 29 | CH(OC₂H₅)₂ | n-C₃H₇ | (E)—CH₂—CH=CHCl | |
| 30 | CH(OC₂H₅)₂ | n-C₃H₇ | (E)—CH₂—CH=CHCH₃ | |
| 31 | CH(OC₄H₉)₂ | C₂H₅ | C₂H₅ | |
| 32 | CH(OC₄H₉)₂ | C₂H₅ | CH₂—CH=CH₂ | |
| 33 | CH(OC₄H₉)₂ | C₂H₅ | (E)—CH₂—CH=CHCl | |
| 34 | CH(OC₄H₉)₂ | C₂H₅ | (E)—CH₂—CH=CHCH₃ | |
| 35 | CH(OC₄H₉)₂ | n-C₃H₇ | C₂H₅ | |
| 36 | CH(OC₄H₉)₂ | n-C₃H₇ | CH₂—CH=CH₂ | |
| 37 | CH(OC₄H₉)₂ | n-C₃H₇ | (E)—CH₂—CH=CHCl | |
| 38 | CH(OC₄H₉)₂ | n-C₃H₇ | (E)—CH₂—CH=CHCH₃ | |
| 39 | CH(OCH₃)₂ | n-C₃H₇ | n-C₃H₇ | 0.99(t), 3.34(s), 4.04(t), 5.37(s) |
| 40 | CH(OCH₃)₂ | n-C₃H₇ | CH₂—C≡CH | 0.97(t), 3.34(s), 4.66(d), 5.34(s) |
| 41 | CHO | n-C₃H₇ | 5-chloro-2-thenyl | |
| 42 | CHO | C₂H₅ | 5-chloro-2-thenyl | |
| 43 | CH(OCH₃)₂ | n-C₃H₇ | 5-chloro-2-thenyl | |
| 44 | CH(OCH₃)₂ | C₂H₅ | 5-chloro-2-thenyl | |
| 45 | CH(OCH₂CH₂OCH₃)₂ | n-C₃H₇ | C₂H₅ | |
| 46 | CH(OCH₂CH₂OCH₃)₂ | C₂H₅ | (E)—CH₂—CH=CH—CH₃ | |
| 47 | CH(OCH₂CH₂SCH₂CH₃)₂ | n-C₃H₇ | C₂H₅ | |
| 48 | CH(OCH₂CH₂SCH₂CH₃)₂ | C₂H₅ | CH₂—CH=CH₂ | |
| 49 | CH(OCH₂CH₂Cl)₂ | n-C₃H₇ | C₂H₅ | |
| 50 | CH(OCH₂CH₂Cl)₂ | n-C₃H₇ | CH₂—CH=CH₂ | |
| 51 | CH(OCH₂CH₂Cl)₂ | n-C₃H₇ | (E)—CH₂—CH=CH—Cl | |
| 52 | CH(OCH₂CH₂Cl)₂ | C₂H₅ | C₂H₅ | |
| 53 | CH(OCH₂CH₂Cl)₂ | C₂H₅ | (E)—CH₂—CH=CH—CH₃ | |
| 54 | CH(OCH₂CCl₃)₂ | C₂H₅ | (E)—CH₂—CH=CH—CH₃ | |
| 55 | CH(OCH₂CH₂CH₂Br)₂ | n-C₃H₇ | C₂H₅ | |
| 56 | CH(OCH₂CH₂CH₂Br)₂ | C₂H₅ | (E)—CH₂—CH=CH—Cl | |
| 57 | CH(OCH₂CF₂CF₂CF₃)₂ | n-C₃H₇ | (E)—CH₂—CH=CH—Cl | |
| 58 | CH(OCH₂CF₂CF₂CF₃)₂ | C₂H₅ | (E)—CH₂—CH=CH—CH₃ | |
| 59 | CH(OCH(CH₃)CH₂OCH₃)₂ | C₂H₅ | C₂H₅ | |
| 60 | CH(SCH₃)₂ | n-C₃H₇ | C₂H₅ | 0.99(t), 1.32(t), 2.1(s), 4.79(s) |
| 61 | CH(SCH₃)₂ | n-C₃H₇ | (E)—CH₂—CH=CH—CH₃ | 0.99(t), 2.1(t), 4.47(d), 4.79(s) |
| 62 | CH(SCH₃)₂ | n-C₃H₇ | (E)—CH₂—CH=CH=Cl | 0.98(t), 2.11(s), 4.56(d), 4.78(s) |
| 63 | CH(SCH₃)₂ | C₂H₅ | C₂H₅ | 69–71 |
| 64 | CH(SCH₃)₂ | C₂H₅ | n-C₃H₇ | |
| 65 | CH(SCH₂CH₃)₂ | C₂H₅ | C₂H₅ | 1.17(t, 3H), 1.23(t, 6H), 1.34(t, 3H), 4.1(q, 2H), 4.92(s, 1H) |
| 66 | CH(SCH₂CH₃)₂ | n-C₃H₇ | C₂H₅ | 1.0(t, 3H), 1.26(t, 6H), 1.36(t, 3H), |

TABLE-continued

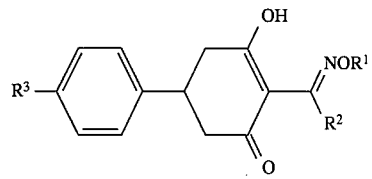

(I)

| Comp. no. | $R^3$ | $R^2$ | $R^1$ | m.p. [°C.] or characteristic $^1$H-NMR data [δ ppm] |
|---|---|---|---|---|
| 67 | $CH(SCH_2CH_2CH_3)_2$ | $n-C_3H_7$ | $C_2H_5$ | 1.61("6", 2H), 4.16(q, 2H) |
| 68 | $CH(SCH_2CH_2CH_3)_2$ | $C_2H_5$ | (E)—$CH_2$—$CH$=$CH$—$CH_3$ | 0.95(t), 1.14(t), 4.47(d), 4.86(s) |
| 69 | $CH(SCH_2CH_2CH_3)_2$ | $n-C_3H_7$ | $C_2H_5$ | |
| 70 | $CH(SCH_2CH_2CH_3)_2$ | $n-C_3H_7$ | $CH_2$—$C$≡$CH$ | |
| 71 | $CH(SCH_2CH_2SCH_2CH_3)_2$ | $n-C_3H_7$ | (E)—$CH_2$—$CH$=$CH$—$CH_3$ | |
| 72 | $CH(SCH_2CH_2SCH_2CH_3)_2$ | $C_2H_5$ | (E)—$CH_2$—$CH$=$CH$—$Cl$ | |
| 73 | $CH(SCH_2CH_2OCH_2CH_3)_2$ | $C_2H_5$ | (E)—$CH_2$—$CH$=$CH$—$CH_3$ | |
| 74 | $CH(SCH_2CH_2OCH_2CH_3)_2$ | $n-C_3H_7$ | $CH_2$—$CH$=$CH_2$ | |
| 75 | $CH(SCH_2CH_2CH_2Cl)_2$ | $n-C_3H_7$ | $C_2H_5$ | |
| 76 | $CH(SCH_2CH_2CH_2Cl)_2$ | $C_2H_5$ | $CH_2$—$CH$=$CH_2$ | |
| 77 | $CH(SCH_2CH_2CN)_2$ | $n-C_3H_7$ | (E)—$CH_2$—$CH$=$CH$—$Cl$ | |
| 78 | $CH(SCH_2CH_2CN)_2$ | $C_2H_5$ | (E)—$CH_2$—$CH$=$CH$—$CH_3$ | |
| 79 | $CH[SCH_2CH_2N(CH_3)_2]_2$ | $n-C_3H_7$ | $C_2H_5$ | |
| 80 | $CH[SCH_2CH_2N(CH_3)_2]_2$ | $C_2H_5$ | $C_2H_5$ | |
| 81 | 1,3-dioxan-2-yl | $n-C_3H_7$ | $C_2H_5$ | 94–95 |
| 82 | 1,3-dioxan-2-yl | $C_2H_5$ | (E)—$CH_2$—$CH$=$CH$—$Cl$ | |
| 83 | 4,4-dimethyl-1,3-dioxan-2-yl | $n-C_3H_7$ | $n-C_3H_7$ | |
| 84 | 4,4-dimethyl-1,3-dioxan-2-yl | $C_2H_5$ | $CH_2$—$CH$=$CH_2$ | |
| 85 | 4-chloromethyl-1,3-dioxan-2-yl | $n-C_3H_7$ | $C_2H_5$ | |
| 86 | 4-chloromethyl-1,3-dioxan-2-yl | $n-C_3H_7$ | (E)—$CH_2$—$CH$=$CH$—$CH_3$ | |
| 87 | 4-chloromethyl-1,3-dioxan-2-yl | $C_2H_5$ | $C_2H_5$ | |
| 88 | 4-methylthioethyl-1,3-dioxan-2-yl | $n-C_3H_7$ | $C_2H_5$ | |
| 89 | 4-hydroxymethyl-1,3-dioxan-2-yl | $n-C_3H_7$ | $C_2H_5$ | |
| 90 | 4-hydroxymethyl-1,3-dioxan-2-yl | $C_2H_5$ | $C_2H_5$ | |
| 91 | 1,3-dithiolan-2-yl | $n-C_3H_7$ | $C_2H_5$ | 0.99(t, 3H), 1.34(t, 3H), 1.61(m, 2H), 4.12(g, 2H), 5.66(s, 1H) |
| 92 | 1,3-dithiolan-2-yl | $n-C_3H_7$ | $CH_2$—$CH$=$CH_2$ | 1.01(t, 3H), 1.62(m, 2H), 4.58(d, 2H), 5.67(s, 1H) |
| 93 | 1,3-dithiolan-2-yl | $C_2H_5$ | (E)—$CH_2$—$CH$=$CH$—$CH_3$ | 97–98 |
| 94 | 1,3-dithiolan-2-yl | $C_2H_5$ | (E)—$CH_2$—$CH$=$CH$—$Cl$ | 72–75 |
| 95 | 4-methyl-1,3-dithiolan-2-yl | $C_2H_5$ | $C_2H_5$ | |
| 96 | 1,3-oxothiolan-2-yl | $n-C_3H_7$ | $C_2H_5$ | |
| 97 | 1,3-dithiolan-2-yl | $n-C_3H_7$ | $CH_2$—$C$≡$CH$ | |
| 98 | 1,3-dithiolan-2-yl | $n-C_3H_7$ | (E)—$CH_2$—$CH$=$CH$—$CH_3$ | |
| 99 | 5,5-dimethyl-1,3-dioxan-2-yl | $n-C_3H_7$ | $C_2H_5$ | 94–95 |
| 100 | 5,5-dimethyl-1,3-dioxan-2-yl | $n-C_3H_7$ | (E)—$CH_2$—$CH$=$CH$—$Cl$ | 99–100 |
| 101 | 1,3-dioxan-2-yl | $n-C_3H_7$ | $CH_2$—$CH$=$CH_2$ | |
| 102 | 1,3-dioxan-2-yl | $C_2H_5$ | (E)—$CH_2$—$CH$=$CH$—$Cl$ | |
| 103 | 1,3-dioxan-2-yl | $C_2H_5$ | (E)—$CH_2$—$CH$=$CH$—$CH_3$ | |
| 104 | 4,4,6-trimethyl-1,3-dioxan-2-yl | $n-C_3H_7$ | $C_2H_5$ | |
| 105 | 4,4,6-trimethyl-1,3-dioxan-2-yl | $C_2H_5$ | $C_2H_5$ | |
| 106 | 5-methoxymethyl-5-methyl-1,3-dioxan-2-yl | $n-C_3H_7$ | $C_2H_5$ | |
| 107 | 1,3-dithian-2-yl | $n-C_3H_7$ | $C_2H_5$ | 1.0(t), 1.33(t), 4.11(q), 5.17(s) |
| 108 | 1,3-dithian-2-yl | $n-C_3H_7$ | (E)—$CH_2$—$CH$=$CH$—$Cl$ | 1.0(t), 4.52(d), 5.18(s) |
| 109 | 1,3-dithian-2-yl | $C_2H_5$ | $CH_2$—$CH$=$CH_2$ | 78–81 |
| 110 | 1,3-dithian-2-yl | $C_2H_5$ | (E)—$CH_2$—$CH$=$CH$—$CH_3$ | 121–122 |
| 111 | $CH(OCH_3)_2$ $Na^+$ salt | $n-C_3H_7$ | $C_2H_5$ | |
| 112 | 1,3-dithiolan-2-yl | $C_2H_5$ | $CH_2$—$CH$=$CH_2$ | 65–68 |
| 113 | 1,3-dithiolan-2-yl | $C_2H_5$ | $C_2H_5$ | 84–87 |
| 114 | 1,3-dithian-2-yl | $C_2H_5$ | $C_2H_5$ | 143–45 |
| 115 | 1,3-dithian-2-yl | $C_2H_5$ | (E)—$CH_2$—$CH$=$CH$—$Cl$ | 111–14 |
| 116 | $CH(OCH_3)_2$ | $C_2H_5$ | $n-C_3H_7$ | |
| 117 | $CH(OCH_3)_2$ | $C_2H_5$ | $CH_2C$≡$CH$ | 1.18(t, 3H), 3.32(s, 6H), 4.68(d, 2H), 5.39(s, 1H) |
| 118 | $CH(OCH_3)_2$ | $n-C_3H_7$ | $CH_2C$≡$CCH_3$ | 0.97(t, 3H), 3.35(s, 6H), 5.38(s, 1H) 7.26(d, 2H), 7.44(d, 2H) |
| 119 | $CH(SCH_3)_2$ | $C_2H_5$ | $CH_2CH$=$CH_2$ | 1.2(t, 3H), 2.11(s, 6H), 4.59(d, 2H), |

TABLE-continued

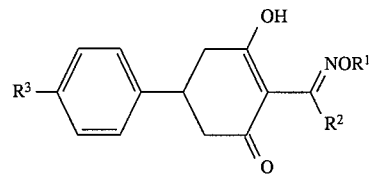

| Comp. no. | R³ | R² | R¹ | m.p. [°C.] or characteristic ¹H-NMR data [δ ppm] |
|---|---|---|---|---|
| 120 | CH(SCH₃)₂ | C₂H₅ | CH₂CH=CHCH₃ | 4.8(s, 1H) 1.17(t, 3H), 1.79(d, 3H), 2.12(s, 6H), 4.79(s, 1H) |
| 121 | CH(SCH₃)₂ | C₂H₅ | CH₂CH=CHCl | 1.18(t, 3H), 2.12(s, 6H), 4.56(d, 2H), 4.79(s, 1H) |
| 122 | CH(SCH₃)₂ | n-C₃H₇ | CH₂CH=CH₂ | 0.98(t, 3H), 2.12(s, 6H), 4.56(d, 2H), 4.77(s, 1H), 5.87–6.08(m, 1H) |
| 123 | 1,3-dioxan-2-yl | n-C₃H₇ | CH₂CH=CHCH₃ | 84–85 |
| 124 | 1,3-dioxan-2-yl | n-C₃H₇ | CH₂CH=CHCl | 78–80 |
| 125 | 1,3-dioxan-2-yl | n-C₃H₇ | CH₂CH=CHCH₃ | 108–110 |
| 126 | 5,5-dimethyl-1,3-dioxan-2-yl | C₂H₅ | C₂H₅ | 115–116 |

The herbicidal agents may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.01 to 3.0, preferably 0.05 to 1.0, kg/ha.

The action of the active ingredients of the formula I on the growth of plants is illustrated in greenhouse experiments.

The vessels employed were plastic flowerpots having a volume of 300 cm³ and filled with a sandy loam containing about 3.0% humus. The seeds of the test plants were sown separately, according to species.

For the preemergence treatment, the formulated active ingredients were then immediately applied to the soil surface. They were suspended or emulsified in water as vehicle and sprayed through finely distributing nozzles. The application rate was 0.5 kg/ha.

After the agents had been applied, the vessels were lightly sprinkler-irrigated to induce germination and growth. The vessels were then covered with transparent plastic hoods until the plants had taken root. This cover ensured uniform germination of the test plants, insofar as this was not impaired by the active ingredients.

For the postemergence treatment, the plants were grown to a height of from 3 to 15 cm, depending on growth form, before being treated. For this treatment, either plants which had been sown in the pots and grown there were selected, or they were cultivated separately as seedlings and transplanted to the pots a few days before being treated. The application rates were 0.06, 0.125 and 0.25 kg/ha. No covers were placed on the vessels in this treatment method.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed.

The assessment scale was 0 to 100, 100 denoting non-emergence or complete destruction of at least the visible plant parts, and 0 denoting no damage or normal growth.

The plants used in the greenhouse experiments belonged to the following species:

| Abbreviation | Botanical name | Common name |
|---|---|---|
| AVEFA | *Avena fatua* | wild oats |
| ALOMY | *Alopecurus myosuroides* | blackgrass |
| BROIN | *Bromus inermis* | smooth broome |
| DIGSA | *Digitaria sanguinalis* | large crabgrass |
| LOLMU | *Lolium multiflorum* | annual ryegrass |
| MEDSA | *Medicago sativa* | alfalfa |
| SETIT | *Setaria italica* | foxtail millet |
| SETVI | *Setaria viridis* | green foxtail |
| SINAL | *Sinapis alba* | white mustard |
| TRZAS | *Triticum aestivum* | wheat |
| TRZAW | *Triticum aestivum* | wheat |
| ZEAMX | *Zea mays* | Indian corn |

Compounds nos. 8, 111 and 19 are suitable for combating grassy vegetation on postemergence application of 0.25 kg/ha. Broadleaved crops, for example alfalfa, are not damaged. The novel active ingredients have a selective herbicidal action (Table 1).

Compound no. 8 may be used postemergence for combating unwanted grasses in wheat. Damage to the crop plants is slight, if any at all (Table 2).

Compounds nos. 8 and 19, when applied preeemergence at 0.5 kg/ha, have a strong herbicidal action on grassy plants; mustard, an example of a broadleaved species, remains undamaged (Table 3).

Compounds nos. 3 (Table 4) and 4 (Table 5) also combat unwanted grasses. Damage to wheat plants is extremely slight, if any at all. Compounds nos. 5 and 17 (Table 6) also combat unwanted grassy plants, without damaging alfalfa, as an example of a broadleaved crop.

TABLE 1

Herbicidal action on unwanted grassy plants and tolerance by a crop on postemergence application of 0.25 kg/ha in the greenhouse

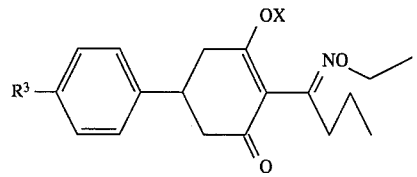

| Comp. no. | R³ | X | MEDSA | AVEFA | BROIN | LOLMU | ZEAMX* |
|---|---|---|---|---|---|---|---|
| 8 | CHO | H | 0 | 100 | 95 | 100 | 100 |
| 111 | CH(OCH₃)₂ | Na | 0 | 100 | 98 | 98 | 98 |
| 19 | CH(OCH₃)₂ | H | 0 | 100 | 98 | 100 | 100 |

*as volunteer corn

TABLE 2

Herbicidal action on unwanted grassy plants and tolerance by a crop on postemergence application in the greenhouse

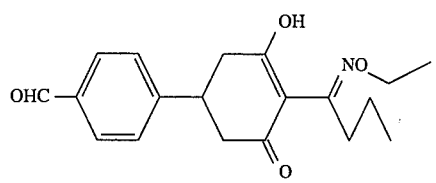

| | | Test plants and damage (%) | | |
|---|---|---|---|---|
| Comp. no. | kg/ha | TRZAS* | ALOMY | AVEFA |
| 8 | 0.06 | 5 | 98 | 95 |

*Schirokko variety

TABLE 3

Herbicidal action on unwanted grassy plants and tolerance by a broadleaved unwanted plant on preemergence application of 0.5 kg/ha in the greenhouse

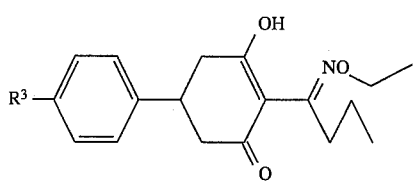

| | | Test plants and damage (%) | |
|---|---|---|---|
| Comp. no. | R³ | SINAL | LOLMU |
| 8 | CHO | 0 | 100 |
| 19 | CH(OCH₃)₂ | 0 | 100 |

Examples illustrating the control of unwanted grassy plants and tolerance by a crop on postemergence application of 0.125 kg/ha in the greenhouse

TABLE 4

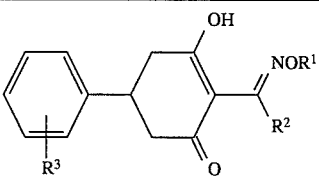

| Comp. no. | R₁ | R₂ | R₃ | TRZAS | LOLMU | DIGSA |
|---|---|---|---|---|---|---|
| 3 | CH₂CH=CH₂ | C₂H₅ | 4-CHO | 10 | 100 | 95 |

TABLE 5

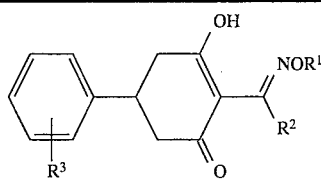

| Comp. no. | $R_1$ | $R_2$ | $R_3$ | TRZAS | DIGSA | SETIT |
|---|---|---|---|---|---|---|
| 4 | (E)—$CH_2CH$=CHCl | $C_2H_5$ | 4-CHO | 0 | 95 | 100 |

TABLE 6

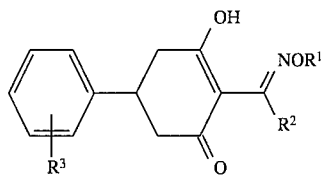

| Comp. no. | $R_1$ | $R_2$ | $R_3$ | MEDSA | LOLMU | DIGSA | SETVI |
|---|---|---|---|---|---|---|---|
| 5 | (E)—$CH_2CH$=$CHCH_3$ | $C_2H_5$ | 4—CHO | 0 | 100 | 100 | 100 |
| 17 | (E)—$CH_2CH$=CHCl | $C_2H_5$ | 4—$CH(OCH_3)_2$ | 0 | 100 | 98 | 100 |

In view of the spectrum of weeds that can be combated, the tolerance of the active ingredients by crop plants or the desired influence of their growth, and in view of the numerous application methods possible, the compounds according to the invention may be used in a large number of crop plants. Examples are given below:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |

-continued

| Botanical name | Common name |
|---|---|
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Ables alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |

| Botanical name | Common name |
| --- | --- |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, maize |

To increase the spectrum of action and to achieve synergistic effects, the active ingredients of the formula I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, cyclohexenones, triazinones, uracils, benzofuran derivatives, quinolinecarboxylic acids, (hetero)-aryloxyphenoxypropionic acids, their salts, esters and amides, etc.

It may also be useful to apply the active ingredients of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone compound of the formula I

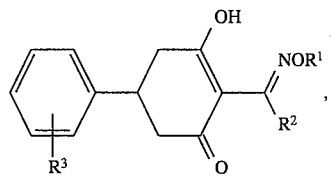

(I)

where $R^1$ is alkyl of 1 to 4 carbon atoms, alkenyl or alkynyl of 3 or 4 carbon atoms, haloalkenyl of 3 or 4 carbon atoms and 1 to 3 halogen substituents, or is thenyl which is unsubstituted or mono-, di- or trisubstituted by halo and/or $C_1$–$C_4$-alkyl, $R^2$ is alkyl of 1 to 4 carbon atoms, and $R^3$ is formyl, a radical of the general formula $R^4XCHXR^5$, where X is oxygen or sulfur, and $R^4$ and $R^5$ are identical or different alkyl, or together denote alkylene of 1 to 4 carbon atoms and which is unsubstituted or substituted by $C_1$–$C_4$-alkyl, $C_1$–$C_4$-alkoxy, $C_1$–$C_4$-alkylthio, hydroxy, halogen, cyano or $C_1$–$C_4$-dialkylamino, and their biologically active salts with alkali metal, alkaline earth metal and ammonium ions and esters thereof with $C_1$–$C_{10}$-carboxylic acids or inorganic acids, and wherein the $R_3$ is in the 4-position.

2. A herbicidal composition containing conventional auxiliaries and a herbicidally effective amount of a cyclohexenone compound of the formula I as set forth in claim 1.

3. A process for combating the growth of unwanted plants, wherein the unwanted plants and/or the area to be kept free from unwanted plant growth is treated with a herbicidally effective amount of a cyclohexenone compound of the formula I as set forth in claim 1.

4. A cyclohexenone compound of the formula I as defined in claim 1, wherein $R^3$ is formyl, $R^1$ is ethyl and $R^2$ is n-propyl.

5. A process for combating the growth of unwanted plants that are located among winter wheat plants which comprises treating the unwanted plants and/or the area to be kept free from unwanted plants in winter wheat with a herbicidally effective amount of the cyclohexenone compound of claim 4.

* * * * *